United States Patent
Meconi et al.

[11] Patent Number: 5,770,220
[45] Date of Patent: Jun. 23, 1998

[54] ACTIVE SUBSTANCE-CONTAINING PATCH

[75] Inventors: Reinhold Meconi, Neuwied; Frank Seibertz, Bad Hönningen/Ariendorf, both of Germany

[73] Assignee: LTS Lohmann Therapie Systeme GmbH, Neuwied, Germany

[21] Appl. No.: 640,791

[22] PCT Filed: Nov. 23, 1994

[86] PCT No.: PCT/EP94/03866

§ 371 Date: Aug. 5, 1996

§ 102(e) Date: Aug. 5, 1996

[87] PCT Pub. No.: WO95/15158

PCT Pub. Date: Jun. 8, 1995

[30] Foreign Application Priority Data

Dec. 4, 1993 [DE] Germany .......................... 43 41 444.3

[51] Int. Cl.$^6$ .................................................. A61F 13/02
[52] U.S. Cl. .......................................... 424/448; 424/449
[58] Field of Search ..................................... 424/448, 449

[56] References Cited

U.S. PATENT DOCUMENTS

| | | | |
|---|---|---|---|
| 3,598,122 | 8/1971 | Zaffaroni | 424/449 |
| 4,877,618 | 10/1989 | Reed, Jr. | 424/448 |
| 4,911,707 | 3/1990 | Heiber | 424/449 |
| 4,983,395 | 1/1991 | Chang | 424/448 |
| 5,008,110 | 4/1991 | Benecke | 424/448 |
| 5,314,694 | 5/1994 | Gale | 424/448 |

FOREIGN PATENT DOCUMENTS

| | | |
|---|---|---|
| 0208395 | 1/1987 | European Pat. Off. ........ A61M 35/00 |
| 3 315 272 | 3/1986 | Germany . |
| 3 503 111 | 8/1986 | Germany . |
| 3 522 060 | 1/1987 | Germany . |
| 3 843 239 | 2/1990 | Germany . |

*Primary Examiner*—D. Gabrielle Phelan
*Attorney, Agent, or Firm*—Wenderoth, Lind & Ponack

[57] ABSTRACT

An active substance-containing patch for the controlled release of active substances, comprising a backing layer, an adjoining active substance-containing reservoir layer softening at body temperature, a membrane controlling the active substance release, a pressure-sensitive adhesive device permitting fixation of the patch to the skin, and a removable protective layer, is characterized by the fact that the reservoir layer which softens at body temperature is spaced away from the controlling membrane by means of a device made of a material impermeable to the active substance which extends all over the mutually facing surfaces of the reservoir and the membrane and which has at least one passage for the reservoir layer which softens at body temperature.

11 Claims, 1 Drawing Sheet

ACTIVE SUBSTANCE-CONTAINING PATCH

This application is a 371 of PCT/EP94/03866, filled Nov. 23, 1994.

SPECIFICATION

The present invention relates to an active substance-containing patch for the controlled release of active substances, comprising an active substance-containing reservoir mass which softens at body temperature. The present invention further relates to a process for its production.

BACKGROUND OF THE INVENTION

Active substance-containing patches of the mentioned kind have been known for some time.

DE 35 03 111 describes a patch comprising drugs in a solid reservoir mass which softens at body temperature and is formed as a disk. The active substance release starts immediately after application.

Another patch of this kind is described in DE 35 22 060, here a reservoir mass disk is fixed to an elastic plastic disk having the same diameter. The two connected parts are present in a housing that can be fixed to the skin and which is closed on the side away from the skin but open towards the skin surface. The elastic plastic disk exerts constant pressure on the reservoir layer. In this case again, the active substance release starts immediately after application.

However, it is not always desirable that the active substance release sets in immediately after application of the patch. For instance, there may be the medical demand to manufacture a patch wherein the onset of active substance release begins after a defined period from application. This ensures that only part of the wearing period of the patch is available for active substance release. If the patch is changed daily, there are phases without any active substance release alternating with those wherein active substance is delivered to the body. A patch of this kind has not yet been known in the art.

DESCRIPTION OF THE INVENTION

It is accordingly the object of the present invention to provide an active substance-containing patch with an active substance-containing reservoir mass softening at body temperature, which releases the active substance only after a predetermined period from application.

Most surprisingly, it has been found that this object is achieved by the fact that the reservoir layer, which softens at body temperature, is spaced away from a controlling membrane by means of a device made of a material which is impermeable to the active substance and which extends over the complete, mutually facing surfaces of the reservoir and the membrane and has at least one passage for the reservoir layer which softens at body temperature.

Accordingly, the active substance-containing patch for the controlled release of active substances consists of a backing layer, an adjoining reservoir layer softening at body temperature and comprising active substances, a membrane controlling the active substance release, a pressure sensitive adhesive device permitting fixation of the patch to the skin, and a removable protective layer, wherein the reservoir layer softening at body temperature is spaced away from the controlling membrane by means of a device formed according to the present invention and made of a material which is impermeable to the active substance.

The active substance-containing reservoir has the function of accommodating the active substance. It softens after application and thereby makes it possible for the active substance to pass through the device for adjusting the distance to the membrane.

The device for adjusting the distance provides a space between reservoir layer and membrane and thereby prevents their premature contact. This prevents the active substance from reaching the membrane undesirably rapidly or spontaneously, which would cause the onset of active substance release.

The membrane has the function of controlling the active substance release and of ensuring zero-order release.

The device for regulating the distance extends over the whole, mutually facing surfaces of the reservoir and the membrane. It is provided with at least one opening for the reservoir content softening at body temperature and may consist of both a coherent body or component parts not contacting one another.

In this connection, care must be taken that at least one sufficiently large passage is present so that the required active substance amount reaches the membrane. It is also possible, however, to distribute several openings symmetrically or unsymmetrically over the device. These openings may also have the form of slots, for example. In any of these cases, the device forms a coherent unit.

Adjusting the distance may also be achieved by three-dimensional formed pieces, for example, spheres, hemispheres, spherical caps, cuboids, cylinders, and cubes.

Suitable materials of which the device to adjust the distance may consist include metals, natural and/or synthetic and/or organic polymers, or glass. These substances must be impermeable to the active substance. These include, for example, proteins, such as collagen, elastin, albumin, and casein; polysaccharides, such as cellulose and cellulose derivatives, starch and starch derivatives, as well as galactomannan, chitin and pectin; polyethylene, polypropylene, polyester, polyamide, polyurethane, polyisobutylene, polyethylene-acrylic acid-copolymers, polyacrylonitrile, polyvinyl chloride, polyvinylidene chloride, polytetrafluoroethylene, styrene-butadiene-styrene block copolymers, styrene-isoprene-styrene block copolymers, styrene-ethylene-butylene-styrene block copolymers, silicones, acrylonitrile-butadiene-styrene rubber, polycarbonate, polymethyl methacrylate, polyoxyethylene, polyoxymethylene, polystyrene, polyvinyl alcohol, polyvinyl acetate; polysilicic acid, silicates, magnesium-aluminium-silicates, bentonite.

Further materials for the device to adjust the space may be selected from groups consisting of textile fabrics, paper, films, and foamed material. These include, for example, nonwovens, wovens, scrims as well as paper of different qualities and films of different mentioned polymers and metals, as well as foams manufactured from known raw materials.

The reservoir layer softening at body temperature comprises active substances. These include, for example:

atenolol, acinetone, acetylsalicylic acid, aceclidine, amfetaminil, amphetamine, amyl nitrate, apophedrine, atebrin, alprostadil, azulene, arecoline, anethole, amylene hydrate, acetylcholine, acridine, adenosine triphosphoric acid, L-malic acid, alimemazine, allithiamine, allyl-isothiocyanate, aminoethanol, apyzine, apiole, azatadine, alprenolol, ethinazone, batrafen, betahistine, biperidine, beta-acetyldigoxine, bopindolol, benzatropine, bupranolol, benclonidine, buprenorphine, bisnorephedrine, butacetoluide, benactyzine, clonidine, clemastine, carazolol, clenbuterol, camphor, colecalciferol, chloral hydrate, clemastine, chlorobutanol, capsaicin, cyclopentamine, clobutinol, chamazulene, codeine, chlorpromazine, quinine, chlorothymol, cyclophosphamide, cinchocaine, chlorambucil, chlorphenesin, diclofenac, diltiazem, dihydroergotamine, dihydrocristine, dihydrotoxine, dimenhydrinate, diethylamine salicylate, digoxin, dimethocaine, diethyl ethane, divinyl ethane, dexchlorpheniramine, dinoprostone, dixyrazin, etofenamate, ethyleneglycol monosalicylate, ephedrine, ethosuximide, enallylpropymal, emylcamate, erythritol tetranitrate, emetine, enflurane, eucalyptol, ethylmorphine, 5-fluorouracil, fentanyl, fluanisone, fencarbamide, glibenclamide, gallopamile, guaiazulene, hydromorphone, heparin-prodrugs, cardiac glycosides, halothane, hyoscyamine, histamine, hydroxycaine, hexylresorcinol, ibuprofen, isosorbide dinitrate, isosorbide-5-mononitrate, indometacin, isoaminile, isoaminile citrate, iodine, iodoform, ketotifen, ketoprofen, L-thyroxine, levonorgestrel, lobeline, lidocaine, lopirin, levamisole, mosidomine, metoclopramide, metoprolol, methamphetaminil, midodrine, methadone, muscarine agonist, methylprylon, methylphenidate, mephenesin, methylephedrine, meclastine, methopromazine, mesuximide, menthol, methoxyflurane, methylpentynol, metixene, misoprostol, nicotine, nicardipine, nitroglycerin, nifedipine, nicotinic acid-β-butoxyethylene ester, nonivamide, nadolol, norethisterone acetate, nicotine agonist, nicethamide, norpseudoephedrine, estradiol, oxytetracaine, oxprenolol, oxyphenbutazone, oxyquinoline, pilocarpine, prazosin, physostigmine, pindolol, propranolol, prostaglandin, pentagotine, piroxamine, piroxicam, pinene, prolintane, procyclidine, piperazine, pivazide, phensuximide, procaine, phenindamine, pheniramine, promethazine, penetrazol, profenamine, perazine, phenol, pethidine, prenylamine, phenoxybenzamine, ryosidine, resochin, selegeline, soquinolol, salbutamol, scopolamine, salicylic acid ester, sparteine, tamoxifen, tizanidine, testosterone, tilidine, theophylline, trimegestone, trichloroethylene, timolol, trifluoperazine, tetracaine, trimipramine, tranylcypromine, trimethadione, tybamate, thymol, thioridazine, verapamil, valproic acid, yohimbine, and other active substances which can be absorbed via the skin, enclosed mucous membranes, known to the skilled artisan. As a matter of fact, this is not a exclusive listing.

The active substances nitroglycerin, nicotine, estradiol and its pharmaceutically acceptable esters, as well as gestagens and their pharmaceutically acceptable esters are particularly preferred.

The device for adjusting the distance is contacted with the reservoir layer immediately after formation thereof. This may be effected, for example, by inserting or laminating. This process may also be carried out under simultaneous exertion of pressure.

Moreover, the device for distance regulation may be applied on the membrane and then joined with the reservoir layer. This may, for example, be effected such that the membrane is coated or extruded from the melt and then combined with the space-adjusting device.

The controlling membrane is permeable to the active substance. It controls the active substance release. Active substance release is controlled by the thickness and composition of the membrane.

The membrane consists of substances which are permeable to the respective active substance. These may, for example, be polymers, such as ethylene-vinyl-acetate copolymer, polyurethane, polyethylene, polypropylene, polyvinyl alcohol, polyvinyl acetate. These membranes may also be microporous. They have a layer thickness of 0.01 to 10 mm, preferably 0.02 to 0.3 mm.

The controlling membrane may be formed of a pressure-sensitive adhesive layer. Any pressure-sensitive adhesive known to the skilled artisan may be used.

The active substance-containing patch may additionally comprise an elastic pressure element on the skin-averted side of the reservoir layer. This element has the function of exerting pressure on the reservoir layer in the direction of the skin surface so as to increase the contact to the membrane.

The active substance-containing reservoir layer which softens at body temperature may consist of polyethylene glycol, polypropylene glycol ether, polyvinyl alcohol, waxes based on castor oil derivatives, fatty alcohols, fatty alcohol ethers, caprylic/capric acid triglyceride, glycerol monocaprylate, glycerol monolaurate, glycerol monodicaprylate, medium-chain partial glycerides, and mixtures thereof.

The active substance-containing reservoir layer softening at body temperature has a thickness of 0.01 to 1.0 mm.

The period after which the active substance release sets in may be predetermined by several measures. In addition to the device for adjusting the distance, the composition of the reservoir layer and the selection of the membrane are also very important. The viscosity and with it the flow behavior of the reservoir layer which softens at body temperature can be predetermined by the selection of suitable components. Also, the material and the thickness of the membrane make it possible to predetermine the period after which the release starts.

The materials for the impermeable backing layer and the removable protective layer are known to the skilled artisan (e.g. DE 38 43 239).

A supporting layer is also known to the skilled artisan (e.g. DE 38 43 239). The use of a supporting layer may be indicated for reasons of manufacturing technique. This is the case if the active substance-containing reservoir layer which softens at body temperature has an insufficient structural strength for mechanical further processing.

The pressure-sensitive adhesive device serves to fix the patch to the skin. It may have different geometrical shapes and cover the patch either completely or partially. The pressure-sensitive adhesive device may, for instance, be formed of a ring surrounding the active substance-containing reservoir. It may, however, also be formed of a pressure-sensitive adhesive in the form of dots, rhombi, strips, and networks.

The pressure-sensitive adhesive device for fixation to the skin is formed of pressure-sensitive adhesives known to the skilled artisan. These pressure-sensitive adhesive layers have a thickness of 0.01 to 0.9 mm.

A process for the production of the patch is carried out in several steps:

The active substance-containing reservoir layer which softens at body temperature may be a solution, dispersion, suspension, or a melt. It is preferable, however, to produce the reservoir layer from the melt.

To this end, the individual components are melted in a water bath, the active substance is added, and the mixture is homogenized by stirring. The resultant active substance-containing reservoir mass is coated on a supporting layer, laminated with the device for adjusting the distance and then with the membrane. Sheet-like structures are punched from the laminate so obtained. These are placed on a backing layer which is provided with pressure-sensitive adhesive, and the complete article is coated with another pressure-sensitive adhesive layer and then covered with a removable protective layer which is provided with a double-side silicone coating. Sheet-like structures are punched such that the pressure-sensitive adhesive layer projects the active substance-containing reservoir on all sides.

BRIEF DESCRIPTION OF THE DRAWINGS

The present invention will be illustrated in greater detail by the Figures.

In FIG. 1, the active substance is present in the active substance-containing reservoir layer (15) which softens at body temperature; this is positioned on the backing layer (16). The device for adjusting the distance having several passages and being in contact with the reservoir (15) is indicated by (14); the adjoining membrane is represented by (13). A pressure-sensitive adhesive device (12) extending over the whole surface and being covered by the removable protective layer (11) is in contact with the membrane.

In FIG. 2, the active substance-containing reservoir layer (25) softening at body temperature is in contact with the elastic pressure element (26) which is positioned on the backing layer (27). The distance-adjusting device (24), again having several openings, is in contact with the reservoir layer (25) and connected with the membrane (23) on the opposite side. The surrounding pressure-sensitive adhesive device (22) is in contact with the membrane (23) and covered with the removable protective layer (21).

EXAMPLE 1

Figure 1:
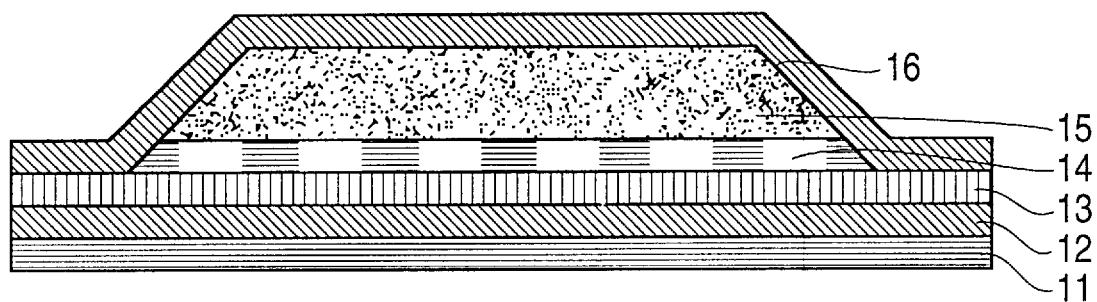
FIGS. 1 and 2 show not-to-scale cross sections through patches according to the present invention.
Figure 2:
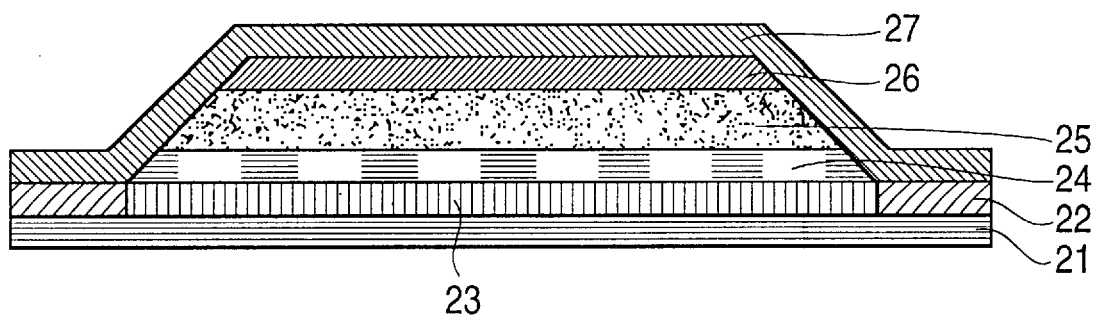

The reservoir layer softening at body temperature is produced as follows:

| | |
|---|---|
| 350 g | polyethylene glycol 600 (Merck) |
| 150 g | polyethylene glycol 1000 (Merck) are melted in the water bath at 50° C. and then |
| 500 g | nitroglycerin-lactose-trituration (10% nitroglycerin, Dynamit Nobel) is added, followed by homogenizing through stirring. |

The nitroglycerin-containing reservoir mass so obtained is coated on a supporting layer of a polyethylene terephthalate film (Hostaphan RN 36, Hoechst) in such a manner that an active substance-containing reservoir layer having a weight per unit area of about 225 g/m$^2$ results. Subsequently, a nonwoven (Paratex III/40, Lohmann) is laminated on this reservoir layer as the device for adjusting the distance, and then a membrane of ethylene-vinylacetate copolymer (0.05 mm, MSP987192, 3M) is laminated thereon.

Disks having an area of 16 cm$^2$ are punched out of the resulting laminate consisting of supporting layer, reservoir layer, device for adjusting the distance, and membrane. A backing layer (Hostaphan RN 15, Hoechst) provided with 20 g/m$^2$ pressure-sensitive adhesive based on polyacrylate (Durotak 280-2516, National Starch) is applied on these disks, and the whole structure is coated with a 100 g/m$^2$ pressure-sensitive adhesive layer based on polyacrylate (Durotak 280-2516, National Starch) and then covered with a removable protective layer of polyethylene terephthalate (Hostaphan RN 100, Hoechst) which is coated with silicone on both sides.

Disks are punched out in such a manner that the pressure-sensitive adhesive layer projects the active substance-containing reservoir on all sides by about 5 mm.

The active substance release is measured as follows:

The active substance patch is shaken in a screw cap jar with 80 ml physiological saline at 32° C. (skin temperature), and samples are measured colorimetrically after given time intervals.

EXAMPLE 2

The active substance-containing reservoir mass is manufactured as described in Example 1 and has the following composition:

| | |
|---|---|
| 450 g | glycerol ester of the fatty acids $C_{10}$ to $C_{18}$ (Witepsol H 32, Dynamit Nobel), |
| 500 g | nitroglycerin-lactose-trituration (10% nitroglycerin, Dynamit Nobel), and |
| 50 g | caprylic/capric acid-triglyceride (Miglyol 812, Dynamit Nobel). |

The active substance patch is produced as in Example 1, i.e., using a microporous membrane of polyethylene already combined with the device for adjusting the distance in the form of a polypropylene nonwoven (total thickness: 0.075 mm, Celgard 5550,Celanese).

EXAMPLE 3

The active substance-containing reservoir layer is produced as in Example 1, however the following raw materials are used:

| | |
|---|---|
| 450 g | mixture of tri- and partial glycerides of the fatty acids $C_8$ to $C_{18}$ (Softisan 601, Dynamit Nobel), |
| 500 g | nitroglycerin-lactose-trituration (10% nitroglycerin, Dynamit Nobel), and |
| 50 g | caprylic/capric acid-triglyceride (Miglyol 812, Dynamit Nobel). |

The active substance patch is produced as in Example 1, i.e., using a microporous membrane of polyethylene already combined with the device for adjusting the distance (total thickness: 0.13 mm, Celgard 5551, Celanese).

The active substance release of the patch according to Example 1 can be observed after 7 hours. After 24 hours, 0.82 mg of nitroglycerin has been released.

In Example 2, the first active substance delivery can be observed after 3 hours, with 2.21 mg of nitroglycerin being released after 24 hours.

In Example 3, the active substance release starts after 3 hours. After 24 hours, 2.36 mg of nitroglycerin has been released. In a multi-layer nitroglycerin-containing matrix system according to DE 33 15 272 (Example 1), the active substance release starts immediately.

We claim:

1. In an active substance-containing patch for the controlled release of an active substance, said patch comprising a backing layer, an adjoining active substance-containing reservoir layer which softens at body temperature, a membrane controlling the active substance release, a pressure-sensitive adhesive device permitting fixation of the patch to the skin, and a removable protective layer, the improvement wherein the reservoir layer which softens at body temperature is spaced away from the controlling membrane by means of a device made of a material impermeable to the active substance which device extends over all the mutually facing surfaces of the reservoir and the membrane and which device has at least one passage for the reservoir layer which softens at body temperature.

2. An active substance-containing patch according to claim 1 wherein the device for adjusting the distance consists of a coherent structure.

3. An active substance-containing patch according to claim 1 or 2 wherein the device for adjusting the distance consists of component parts not contacting one another.

4. An active substance-containing patch according to claim 1 or 2 wherein the device for adjusting the distance consists of metals, natural and/or synthetic inorganic and/or organic polymers, or of glass.

5. An active substance-containing patch according to claim 1 or 2 wherein the device for adjusting the distance is selected from the group consisting of textile fabrics, paper, films and foam.

6. An active substance-containing patch according to claim 3 wherein the individual parts of the device for adjusting the distance consist of three-dimensional formed pieces.

7. An active substance-containing patch according to claim 1 wherein the reservoir layer softening at body temperature comprises an active substance selected from the group consisting of nitroglycerine, nicotine and its pharmaceutically acceptable salts, estrogens and their pharmaceutically acceptable esters.

8. An active substance-containing patch according to claim 1 wherein the controlling membrane is formed of a pressure-sensitive adhesive layer.

9. An active substance-containing patch according to claim 1 wherein an elastic pressure element is present on the skin-averted side of the reservoir layer.

10. In a process for the production of an active substance-containing patch according to claim 1, the improvement wherein the device for adjusting the distance is contacted with the reservoir layer immediately after formation of said reservoir layer.

11. A process for the production of an active substance-containing patch according to claim 10 wherein the device for adjusting the distance is applied on the controlling membrane and then joined with the reservoir layer.

* * * * *